United States Patent [19]

Muto

[11] 4,246,897
[45] Jan. 27, 1981

[54] TRACHEOTOMY OBTURATOR AND TUBE FLANGE

[76] Inventor: Rudolph Muto, 24 Williams St., Andover, Mass. 01810

[21] Appl. No.: 12,198

[22] Filed: Feb. 15, 1979

[51] Int. Cl.³ .................... A61M 16/00; A61M 25/00
[52] U.S. Cl. .................................. 128/207.15; 128/343
[58] Field of Search ............................... 128/348–351, 128/208, 341, 207.14, 207.15, 207.17, 200.26, 343

[56] References Cited

U.S. PATENT DOCUMENTS

| | | | |
|---|---|---|---|
| 1,878,671 | 9/1932 | Cantor | 128/343 |
| 3,087,493 | 4/1963 | Schossow | 128/351 |
| 3,499,450 | 3/1970 | Rathjen | 128/351 |
| 3,693,624 | 9/1972 | Shiley et al. | 128/351 |
| 4,170,232 | 10/1979 | Khoury | 128/351 |

Primary Examiner—Dalton L. Truluck
Attorney, Agent, or Firm—Pearson & Pearson

[57] ABSTRACT

A removable, disposable tracheotomy obturator of soft, plastic material, of the type having a valve plug connected by a flexible strap to a valve cap, normally positioned within a curved tracheotomy tube, is provided with windpipe means to permit the patient to breathe freely while the tube is being inserted during a tracheotomy. The windpipe means may be air passages in the plug and in the cap or may be a continuous, air conduit of soft plastic extending from a blunt, terminal tip in advance of the plug, through the tube and cap to ambient atmosphere. Inflexible proximal portions are provided on the attachment ears of the tube as a means of suspended fixation of the tube as a bridge over the incision.

17 Claims, 3 Drawing Figures

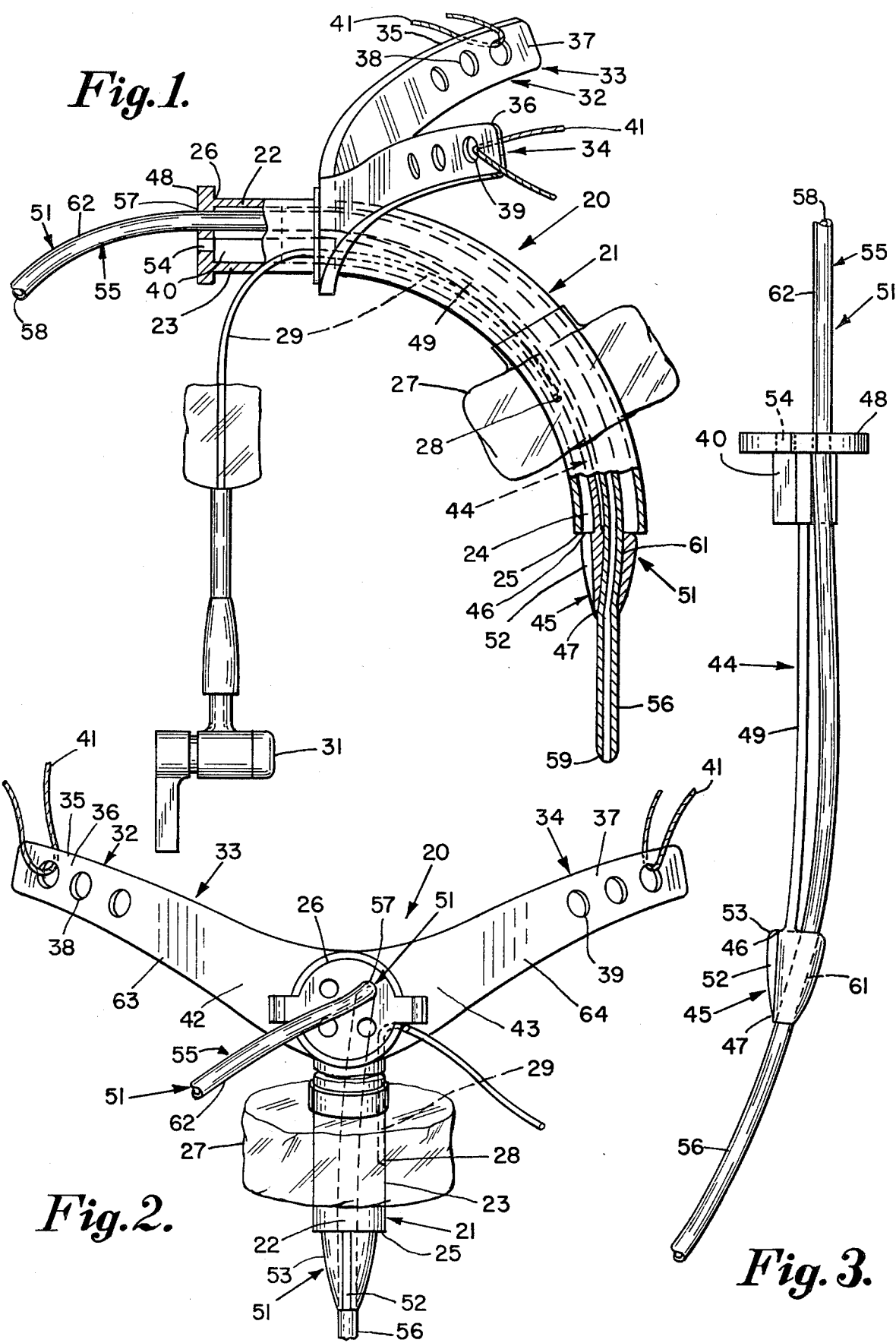

TRACHEOTOMY OBTURATOR AND TUBE FLANGE

BACKGROUND OF THE INVENTION

It has heretofore been proposed to provide an instrument for performing a tracheotomy, the instrument comprising a tube, or cannula, of arcuate configuration and an incisor assembly fitting within the tube. The incisor assembly has comprised a handle, or knob, at the outer end of the tube, a head having a cutting blade projecting from the inner end of the tube and a rod connecting the knob to the cutting head.

Exemplary of such devices are the instruments disclosed in U.S. Pat. No. 2,873,742 to Sheldon of Feb. 17, 1959; U.S. Pat. No. 2,865,374 to Brown of Dec. 23, 1958; and U.S. Pat. No. 3,384,987 to Brummelkamp of Mar. 21, 1968.

The use of sharp cutting blades at the inner end of a tracheal tube in order to make, or enlarge, an incision as the tube is inserted, has been found to have serious disadvantages because the sharp point, or blades, inserted in the front of the trachea may perforate, or damage, the opposite side of the trachea or perforate the gullet lying behind the trachea. Similarly, even more damage could occur in the use of a sharp pointed, hollow needle of hard metal for making the initial incision into the trachea and then withdrawal of the needle for further insertion of the hard cutting edge tip of a trocar, as taught in the Brummelkamp patent. Such instruments are believed to no longer be accepted in modern surgical practice and have become obsolete in favor of tracheal tubes and obturators of soft plastic, inserted, after the incision has been made, by a suitable tracheal spreader.

It has also been proposed to provide a tracheal tube, or guide conduit with an inner expander element telescopically arranged therein for enlarging the incision in the neck. The element having a ball at the tip for attachment of a hollow tubular leader. Such an apparatus is disclosed in U.S. Pat. No. 3,511,243 to Toy on May 12, 1970.

Apparatus for sealing the oesophagus and providing artifical respiration is disclosed in U.S. Pat. No. 3,683,908 to Tantrimudalige et al on Aug. 15, 1972 wherein a curved tube with a cuff is introduced through the mouth, there being a small bore, stomach washing tube extending along the main tube with the outer end connected to a supply of washing water.

None of the above patents disclose a tracheotomy tube with an obturator removably positioned therewithin, the obturator having a valve plug affixed by s strap to a valve cap, and made of relatively soft material free of sharp cutting edges or sharp guide tips and which is provided with air passages permitting the patient to breathe while the device is inserted into the trachea.

SUMMARY OF THE INVENTION

In this invention a tracheal tube and obturator is provided, formed of disposable plastic material, the tracheal tube being free of apertures but having an inflatable cuff proximate its inner end and a pair of attachment ears proximate its outer end.

Unlike prior art devices, the pair of ears have distal sections which are relatively flexible and have proximal sections which are relatively inflexible. Thus, the inflexible central portion, through which the tube extends, is able to bridge an incision without twist, deformation, or distortion when the device is fully inserted and tied around the neck of a patient.

Unlike prior art devices the integral valve plug, valve cap and strap connection therebetween, forming the slidable removable obturator, are formed of relatively soft plastic free of knives, blades, cutting edges, or needle points. However, the obturator of the invention permits a patient to breathe freely during insertion of the tube into an incision and into the trachea by reason of what is termed windpipe means built into the obturator. The windpipe means serves as an auxiliary windpipe for the patient and may consist of air passages in the valve plug and air passages in the valve cap or may consist of a continuous, flexible air conduit extending from a flexible leader in advance of the plug, along the interior of the tube to a free outer end in rear of the cap or both. The air passages in the valve plug are preferably a set of axially extending grooves in the exterior surface thereof and the air passages in the cap are preferable axially extending apertures therein.

BRIEF DESCRIPTION OF THE DRAWING

FIG. 1 is a side elevation, with parts broken away, of a tracheal tube and obturator of the invention;

FIG. 2 is a rear elevation of the device shown in FIG. 1 and;

FIG. 3 is a side elevation of the preferred form of the obturator of the invention.

DESCRIPTION OF THE PREFERRED EMBODIMENT

As shown in the drawing, the tracheotomy tube device 20 of the invention includes a hollow tube 21, of arcuate, or curved, configuration, formed of disposable, relatively soft material 22, such as plastic, and having a wall 23, an interior, or axial bore, 24, an inner end 25 and an outer end 26. The wall 23 of tube 20 is free of apertures except that there is an inflatable cuff 27 of well known type proximate the inner end 25 which is inflatable through an aperture 28 by a small bore, flexible tube 29, through the valve 31, all in a known manner.

A pair 32 of integral, oppositely disposed ears 33 and 34 are located proximate the outer end 26 of tube 21, each formed of plastic material 35. The distal sections 36 and 37 each have tie holes 38 and 39 for ties 41 by which the tracheotomy tube 21 may be held in place around the neck of a patient. The distal sections 36 and 37 of the ears 33 and 34 are of relatively flexible material but the proximal sections 42 and 43 are of relatively inflexible material.

Thus when the tracheal tube 21 is in place with the inner end 25 well down into the trachea of a patient and the outer end 26 projecting from the incision the proximal sections 42 and 43 of the ears form a relatively rigid, but soft, central support which bridges over the incision and is not subject to twist, distortion, or deformation.

The obturator 44 of the invention, is best shown in FIG. 3, and includes a tapered, streamlined valve plug 45 which closely but slidably, fits within the bore 24 of the inner end 25 of tube 21 at the rearward portion 46 but has a forward nose portion 47 normally projecting therefrom to serve as a guide tip. The valve plug 45 of the tracheotomy tube obturator 44 preferably includes a valve cap 48 covering the outer end 26 of the tube 21, the cap having a shank 40 fitting in bore 24 and being affixed to the plug 45 by a flexible element 49 such as a plastic strap, integral with plug and cap. After making an incision in the neck of a patient, the tube 21, with the obturator 44 positioned therewithin, and with the guide nose 47 projecting in advance of the inner end 25, is inserted into the trachea. It will be seen that during such insertion the windpipe, or trachea, of the patient is blocked with conventional tracheotomy devices now in use, and that the patient will gasp, become unduly alarmed and struggle for breath all to the danger of the operation and discomfort of both patient and surgeon.

In this invention windpipe means 51 is provided consisting of air passages, in the plug 45 and air passages in the cap 48. Preferably the air passages in the plug consist of at least one axially extending groove 52 in the exterior surface 53 of the plug 45 and at least one axially extending aperture 54 in the cap 48.

The obturator 44 with its windpipe means 51 is formed of relatively soft, disposable plastic such as nylon, polystyrene or the like and it is free of any sharp points, sharp metallic cutting edges or other incision making blades.

Windpipe means 51 may also be a small bore, flexible plastic, air conduit 55 extending from a flexible, limp, guide leader portion 56 through the center of the plug 45, thence along the interior bore 24 of tube 21 out through aperture 57 in valve cap 48 to an open terminal end 58. Thus air for patient breathing may pass freely from the open terminal inner tip 59 of conduit 55, in advance of plug 45 to the open terminal outer end 58 in rear of cap 48 in the ambient atmosphere.

The conduit 55 is thus available for suction of the contents of the trachea or for introduction of gaseous or liquid fluids, while also performing its auxilliary windpipe function and proving a flexible leader, or guide 56 for the tracheal tube and obturator.

The tip 59 of conduit 55 and the surface 53 of tapered plug 45 are blunt and of soft material so that they are not sharp and likely to damage the trachea. The tapered plug 45 is preferably what I call "olive" shaped and the elongated conduit, or catheter, 55 is preferably slidably received in the aperture 61 in the tip 55 and slidably received in the aperture 57 in the cap 48 so that the length of the flexible leader, or guide, 56 may be adjusted. The leader 56 ranges in length from two to five inches. The portion 62 extending beyond the base, cap, valve or handle 48 to the end 58 is usually about five inches in length and may be connected to a conventional suction valve connected to a specimen collecting buttle.

The wing shaped collar or flange 32, formed by the ears 33 and 34 with its "central curved stiff" portion 42, 43 provides a suspension type of stability to the tracheotomy tube without producing twisting or undue motion of the tube itself and provides stable points away from the surgical incision. In other words a tripod is created consisting of the inflated cuff 27 at the tube inner end 25 and the two outer ends 63 and 64 of the stiff proximal sections 42 and 43 for three points of stability. The tube is thus suspended at points far removed from the incision to prevent twist, prevent inadvertent ejection of the tube and otherwise stabilize the tube.

I claim:

1. A tracheotomy tube device of the type comprising a hollow tube of arcuate configuration with inflatable cuff means proximate the inner end, integral, oppositely disposed, tie ears proximate the outer end and a unitary tracheotomy tube obturator removably positioned within the bore of said hollow tube, said device characterized by:

said unitary tracheotomy obturator having a valve plug with a forward nose of streamlined configuration normally projecting a predetermined distance beyond the inner end of said tube as a guide tip, a valve cap covering the outer end of said tube with a shank fitting within said outer end and a flexible strap connecting said plug to said cap within said tube and integrally attaching said cap to said plug for unitary withdrawal of said obturator;

and said obturator having windpipe means of soft, flexible plastic independent of said strap for conducting air from in advance of said nose, through said curved tube to in rear of said cap;

whereby a patient may breathe freely while said tube device, with its obturator in place, is being inserted through an incision well down into the trachea of a patient.

2. A tracheotomy tube device as specified in claim 1 wherein:

said windpipe means comprises air passages in the said valve plug, the bore of said tube and air passages in the said valve cap of said obturator.

3. A tracheotomy tube device as specified in claim 1 wherein:

said windpipe means comprises an elongated hollow conduit, having an inner portion extending a substantial distance in front of the forward nose of the valve plug of said obturator, said conduit extending from said plug along the interior of said tube alongside said strap and through an aperture in said valve cap to an outer portion;

whereby air may be exhaled or inhaled by a patient during a tracheotomy.

4. A tracheotomy tube device as specified in claim 1 wherein:

said windpipe means comprises air passages in the integral, strap attached valve plug and valve cap of said obturator and the bore of said tube; and an elongated conduit of soft plastic on said obturator slidable in apertures in said valve plug and valve cap for guiding air from in advance of said plug to in rear of said cap as said tracheotomy tube is inserted initially into the trachea.

5. A tracheotomy tube device as specified in claim 1 wherein:

said windpipe means comprises at least one axially-extending groove in the exterior face of said plug, the bore of said tube and at least one axially extending air passage in said cap.

6. A tracheotomy tube device as specified in claim 1 wherein:

said oppositely disposed, tie ears proximate the outer end of said tracheotomy tube each include an inner curved section of relatively inflexible material bridging the incision in a patient's throat to avoid twist of said device and;

each includes an outer section of relatively flexible material for conforming to the shape of the neck of a patient when said device is tied therearound.

7. For use with a tracheotomy tube having an axial bore, a disposable tracheotomy obturator of plastic material comprising:

a valve plug, affixed by a flexible strap to a valve cap; and windpipe means of said material associated with said obturator for conducting air through said valve plug along the axial bore of said tube and through said valve cap to permit a patient to breathe freely when said obturator is in place within a tracheotomy tube.

8. A tracheotomy obturator for use with a tracheotomy tube of disposable, soft, plastic material comprising a guide nose of streamlined configuration having at least one axial extending air passage therein;
 a valve cap having at least one axial extending air passage therein;
 and a flexible strap integrally affixing said nose to said cap to enable said nose to project forwardly of said tube when said obturator is in place in said tube.

9. A tracheotomy obturator of disposable relatively soft material comprising:
 a valve plug having a flexible strap integrally affixed to a valve cap, for unitary extraction from a tracheal tube, and
 windpipe means of said material integral with said plug and cap for permitting a patient to breathe freely along the bore of a tube when said obturator is in place within a tracheotomy tube being inserted into the patient's trachea through a neck incision.

10. A disposable tracheotomy tube and obturator comprising:
 a curved, hollow tracheotomy tube of disposable material having an axial bore; and
 a tracheotomy obturator of a disposable, soft plastic material slidably removable from said tube, said obturator having a valve plug with a forward nose, normally projecting from, the inner end of said tube and a base normally closing the inner end of said tube, a valve cap normally covering, and closing the outer end of said tube and a flexible strap affixing said valve plug to said valve cap;
 and windpipe means of soft plastic material independent of said strap including at least one air passage in said plug and at least one air passage in said cap for conducting air from in advance of said plug along the bore of said tube to in rear of said cap to permit a patient to breathe during a tracheotomy.

11. A tube and obturator as specified in claim 10 wherein:
 said windpipe means includes a hollow conduit of soft, plastic material extending from the ambient atmosphere outside said valve cap, alongside said flexible strap along the bore of said tube, through said valve plug to a free terminal open end substantially beyond said valve plug;
 whereby a patient may inhale and exhale through said conduit as well as along said bore during a tracheotomy.

12. A disposable tracheotomy tube and obturator of the type comprising a curved hollow tube having an axial bore with a removable obturator therewithin said obturator including an imperforate valve plug normally closing the inner end of the tube, an imperforate valve cap normally closing the outer end of the tube and a flexible strap, extending within the bore of said tube, and affixing said plug to said cap characterized by:
 windpipe means of soft, plastic material in said obturator forming an air conduit conducting air independent of said strap from in advance of said plug through said valve plug, through said valve cap to in rear of said cap, during insertion of said tube in the trachea of a patient, to permit the patient to breathe.

13. A disposable tracheotomy tube and obturator as specified in claim 12 wherein:
 said windpipe means comprises axial grooves in said valve plug, the axial bore of said tube and apertures in said valve cap for connecting the trachea of a patient to the ambient atmosphere to continue breathing during insertion of said tube with said obturator in place.

14. A disposable tracheotomy tube and obturator as specified in claim 12 wherein:
 said windpipe means comprises an elongated, flexible air conduit axially slidable within said obturator and extending from an open blunt terminal tip end in advance of said plug, through an aperture in said plug, alongside said strap in said tube and through an aperture in said cap to an opposite open terminal end in rear of said cap.

15. A disposable tracheotomy tube and obturator as specified in claim 12 wherein:
 said windpipe means comprises air passages in said plug connected through the bore of said tube to air passages in said cap; and
 a flexible hollow conduit extending from a blunt terminal tip in advance of said plug, alongside said strap through said tube to in rear of said cap;
 said air passages and said conduit each permitting a patient to breathe while said tube and obturator are being inserted in the trachea.

16. A disposable tracheotomy tube and obturator as specified in claim 12 plus
 a pair of elongated integral ears each extending from an opposite side of said tube proximate said cap, said ears characterized by being of relatively inflexible plastic material at the proximal portions thereof, but of relatively flexible plastic material at the distal portions thereof
 and by each having a plurality of tie holes in each distal portion for use in attachment thereof by a tape around the neck of a patient.

17. A removable, disposable obturator for a tracheotomy tube, said obturator comprising:
 an olive shaped plug having at least one axially extending aperture, forming an air passage, therethrough;
 a, cap having at least one aperture therein forming an air passage therethrough;
 a strap affixing said plug and cap;
 said plug and cap each having a catheter passage independent of said strap for slidably receiving an elongated catheter extending from in advance of said plug alongside said strap in said tube to in rear of said cap;
 whereby said apertures and catheter create air vents and the portion of said catheter in advance of said plug guides said tube into the trachea.

* * * * *